United States Patent [19]
Costantini et al.

[11] Patent Number: 6,040,484
[45] Date of Patent: Mar. 21, 2000

[54] PHENOL COMPOUND HYDROXYLATION METHOD

[75] Inventors: Michel Costantini; Laurent Gilbert; Michel Spagnol, all of Lyons, France

[73] Assignee: Rhodia Chimie, Courbevoie, France

[21] Appl. No.: 09/125,163

[22] PCT Filed: Feb. 5, 1997

[86] PCT No.: PCT/FR97/00223

§ 371 Date: Aug. 13, 1998

§ 102(e) Date: Aug. 13, 1998

[87] PCT Pub. No.: WO97/29066

PCT Pub. Date: Aug. 14, 1997

[30] Foreign Application Priority Data

Feb. 9, 1996 [FR] France .................................. 96 01596

[51] Int. Cl.⁷ .................................................... C07C 37/60
[52] U.S. Cl. .......................... 568/803; 568/771; 568/716; 568/744
[58] Field of Search ..................................... 568/716, 741, 568/735, 744, 771, 803; 502/168

[56] References Cited

U.S. PATENT DOCUMENTS

| | | |
|---|---|---|
| 3,615,169 | 10/1971 | Thom . |
| 4,301,307 | 11/1981 | Jouffret . |
| 4,547,474 | 10/1985 | Olah ......................................... 502/168 |
| 5,434,317 | 7/1995 | Costantini ............................... 568/768 |
| 5,714,641 | 2/1998 | Costantini ............................... 568/768 |

*Primary Examiner*—Paul J. Killos
*Assistant Examiner*—Jean F Vollano
*Attorney, Agent, or Firm*—John Daniel Wood

[57] ABSTRACT

The present invention relates to a process for the hydroxylation of phenolic compounds and, more particularly, to a process for the hydroxylation of phenols and phenolic ethers with hydrogen peroxide. The invention relates to a process for the hydroxylation of phenolic compounds using hydrogen peroxide, said process being characterized in that the reaction is carried out in the presence of an effective quantity of at least one rare earth or bismuth triflate.

42 Claims, No Drawings

PHENOL COMPOUND HYDROXYLATION METHOD

This application is an application under 35 U.S.C. Section 371 of International Application Number PCT/FR97/0023 filed on Feb. 5, 1997.

The present invention relates to a process for the hydroxylation of phenolic compounds and, more particularly, to a process for the hydroxylation of phenols and phenolic ethers with hydrogen peroxide.

Numerous processes for the hydroxylation of phenols are described in the state of the art. The patent FR-A 2 071 464 which relates to a very important industrial process for the hydroxylation of phenols and phenolic ethers may be mentioned amongst others.

The said process consists in carrying out hydroxylation with hydrogen peroxide in the presence of a strong acid. The strong acids most commonly used are sulfuric acid, para-toluene sulfonic acid, and perchloric acid.

The hydroxylation of phenol carried out under the conditions described leads to a mixture of hydroquinone and pyrocatechol, with a predominance of the latter since the hydroquinone/pyrocatechol ratio most often ranges between 0.3 and 0.7.

FR-A 2 266 683 proposed an improvement to this process which consists in carrying out hydroxylation in the presence of a ketone. This results in an improvement in the hydroquinone and pyrocatechol yield of the reaction. However, all the examples described lead to a greater quantity of pyrocatechol compared with that of hydroquinone.

The known processes lead, therefore, mainly to pyrocatechol.

It is apparent that, in order to meet market demand which fluctuates, it is important to have an industrial process which makes it possible either to increase the production of hydroquinone formed with respect to pyrocatechol, or to promote the quantity of pyrocatechol formed.

The applicant proposed, in FR-A 2 667 598, a process which makes it possible to increase the quantity of hydroquinone formed with respect to the quantity of pyrocatechol and to obtain, in its preferential variant, more hydroquinone than pyrocatechol.

The said process consists in carrying out the hydroxylation of phenol in the presence of an effective quantity of a strong acid, said process being characterised in that the reaction is conducted in the presence of a ketone compound chosen from benzophenone and the benzophenones of which the hydrogen atoms of the aromatic nucleus may be substituted by an electro-donor group.

According to the process described in FR-A 2 667 598, the presence of the ketone compound as selected during the hydroxylation of phenol affects the regioselectivity of the reaction, and hydroquinone/pyrocatechol ratios ranging between 1.0 and 1.13 are advantageously obtained.

Pursuing his research, the applicant found another process involving an original catalysis and making it possible to obtain good diphenol yields and to control the selectivity of the reaction.

More specifically, the present invention relates to a process for the hydroxylation of a phenolic compound with hydrogen peroxide, said process being characterised in that the reaction is conducted in the presence of an effective quantity of at least one triflate of rare earth or of bismuth.

A first variant of the process of the invention is to conduct the reaction in the presence of an organic solvent.

A second variant of the process of the invention consists in using a ketone compound as co-catalyst.

A third variant of the process of the invention is to use, at the same time, the co-catalyst and the organic solvent.

In accordance with the process of the invention, hydroxylation of a phenolic compound is carried out in the presence of a catalyst chosen from the triflates of rare earths or of bismuth.

The term "triflate of rare earth or of bismuth" means a rare earth or bismuth salt of trifluoromethane sulfonic acid.

The term "rare earth" means the lanthanides having an atomic number of 57 to 71 and yttrium and also scandium.

The present invention relates to the phenolic compounds having the general formula:

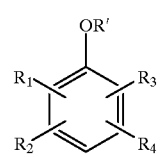

(I)

in which formula (1):

$R_1$, $R_2$, $R_3$ and $R_4$, identical or different, represent a hydrogen atom or any substituent, two groups $R_1$ and $R_2$ and/or $R_3$ and $R_4$ placed on two vicinal carbon atoms may, together and with the carbon atoms bearing them, form a ring, R' represents a hydrogen atom or a hydrocarbon radical having 1 to 24 carbon atoms, which may be a saturated or unsaturated, linear or branched, acyclic aliphatic radical: a monocyclic or polycyclic, saturated or unsaturated cycloaliphatic radical; a saturated or unsaturated, linear or branched aliphatic radical bearing a cyclic substituent.

The term cyclic substituent means a saturated, unsaturated or aromatic carbocycle, generally having 4 to 7 carbon atoms and preferably 6 carbon atoms.

The process of the invention applies to any phenolic compound corresponding to the general formula (I) and, more particularly, to the phenolic compounds of formula (I) in which $R^1$ represents:

a hydrogen atom, a linear or branched alkyl radical having 1 to 6 carbon atoms, preferably 1 to 4 carbon atoms, and more particularly a methyl or ethyl radical, a cyclohexyl radical, a benzyl radical.

The phenolic compound corresponding to formula (I) may bear one or more substituents $R_1$, $R_2$, $R_3$ and $R_4$. Examples of substituents are given below but this list is not limiting. Any substituent may be present on the ring provided that it does not interfere with the desired product.

The process of the invention applies more preferably to the phenolic compounds corresponding to formula (I) in which:

$R_1$, $R_2$, $R_3$ and $R_4$, identical or different, represent $R_0$, one of the following groups:

a hydrogen atom, a linear or branched alkyl radical having 1 to 6 carbon atoms, preferably 1 to 4 carbon atoms such as methyl, ethyl, propyl, isopropyl, butyl, sec-butyl, tert-butyl, a linear or branched alkenyl radical having 2 to 6 carbon atoms, preferably 2 to 4 carbon atoms, such as vinyl, allyl, a linear or branched alkoxy radical having 1 to 6 carbon atoms, preferably 1 to 4 carbon atoms such as the methoxy, ethoxy, propoxy, isopropoxy, butoxy radicals, an acyl group having 2 to 6 carbon atoms,
a radical corresponding to the formula:
—$R_5$—OH
—$R_5$—COO$R_6$
—$R_5$—X
—$R_5$—$CF_3$ in which formulae $R_5$ represents a valency bond or a saturated or unsaturated, linear or branched, divalent hydrocarbon radical having 1 to 6 carbon atoms such as, for example, methylene, ethylene, propylene, isopropylene, isopropylidene, $R_6$ represents a hydrogen atom or a linear or branched alkyl radical having 1 to 6 carbon atoms; X represents a halogen atom, preferably a chlorine, bromine or fluorine atom.

$R_1$, $R_2$, $R_3$ and $R_4$, which may be identical or different, represent $R_7$, one of the following more complex radicals:

a saturated or unsaturated carbocyclic radical having 4 to 7 carbon atoms, preferably a cyclohexyl radical, a radical having the formula

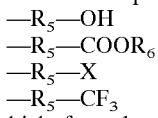

in which $R_5$ represents a valency bond or a saturated or unsaturated, linear or branched, divalent hydrocarbon radical having 1 to 6 carbon atoms such as, for example, methylene, ethylene, propylene, isopropylene, isopropylidene and $R_0$ having the meaning given above and m is an integer from 0 to 4, a radical $R_5$—A—$R_8$ in which $R_5$ has the meaning given above. $R_8$ represents a linear or branched alkyl radical having 1 to 6 carbon atoms or a radical having the formula

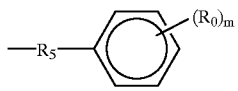

and A represents one of the following groups:

—O—, —COO—, —OCOO—, —$SO_2$—,

in these formulae, $R_9$ represents a hydrogen atom or an alkyl radical having 1 to 4 carbon atoms, a cyclohexyl or phenyl radical, two groups $R_1$ and $R_2$ and/or $R_3$ and $R_4$ placed on two vicinal carbon atoms may, together and with the carbon atoms bearing them, form an unsaturated or aromatic carbocycle having 4 to 7 carbon atoms and preferably 6 carbon atoms.

The compounds corresponding to formula (I) used more particularly are those corresponding to formula (I) in which:
R' represents a hydrogen atom,
$R_1$, $R_2$, $R_3$ and $R_4$, identical or different, represent one of the following groups:
a hydrogen atom,
a linear or branched alkyl radical having 1 to 4 carbon atoms,
a linear or branched alkoxy radical having 1 to 4 carbon atoms,
a hydroxyl group,
a halogen atom,
a —$CF_3$ group,
a cyclohexyl radical,
a phenyl radical,
two groups $R_1$ and $R_2$ and/or $R_3$ and $R_4$ placed on two vicinal carbon atoms may, together and with the carbon atoms bearing them, form a benzene ring.

Even more preferably, the compounds of formula (I) chosen are those in which R' represents a hydrogen atom and one of the radicals $R_1$, $R_2$, $R_3$ and $R_4$ represents a hydroxyl group, a methyl radical or a methoxy radical and the 3 others represent a hydrogen atom.

By way of illustration of the phenolic compounds of formula (I) which may be used in the process of the invention, the following may be mentioned more particularly:

those corresponding to formula (I) in which $R_1$, $R_2$, $R_3$ and $R_4$ represent a hydrogen atom, such as phenol or anisole, those corresponding to formula (I) with a substituent on the benzene ring, such as o-cresol, m-cresol, p-cresol, 2-methoxyphenol, 2-ethylphenol, 3-ethylphenol, 2-propylphenol, 2-sec-butylphenol, 2-tert-butylphenol, 3-tert-butylphenol, 4-tert-butylphenol, 2-methoxyphenol, 3-methoxyphenol, 4-methoxyphenol, methyl salicylate, 2-chlorophenol, 3-chlorophenol, 4-chlorophenol, those corresponding to formula (I) with two substituents on the benzene ring such as 2,3-dimethylphenol, 2,5-dimethylphenol, 2,6-dimethylphenol, 3,5-dimethylphenol, 2,3-dichlorophenol, 2,5-dichlorophenol, 2,6-dichlorophenol, 3,5-dichlorophenol, 2,6-ditert-butylphenol, 3,5-ditert, butylphenol, those corresponding to formula (I) with three substituents on the benzene ring such as 2,3,5-trimethylphenol, 2,3,6-trimethylphenol, 2,3,5-trichlorophenol, 2,3,6-trichlorophenol, those corresponding to formula (I) in which $R_1$ and $R_2$ form a benzene ring, such as 1-hydroxynaphthalene, those corresponding to formula (I) in which $R_1$ represents a radical of the $R_7$ type such as 2-phenoxyphenol, 3-phenoxyphenol.

The phenolic compounds corresponding to formula (I) which may be used in the process of the invention include, on a non-limiting basis, phenol, o-cresol, m-cresol, p-cresol.

The rare earth triflate used as catalyst is, more particularly, a rare earth chosen from the lanthanides, yttrium, scandium and mixtures thereof, preferably the lanthanides such as lanthanum, cerium, praseodymium neodymium, samarium, europium, gadolinium, terbium, dysprosium, holmium, erbium, thulium, ytterbium and lutetium and mixtures thereof.

It is possible to use a mixture of ceric rare earths including the elements La, Ce, Pr, Nd and/or yttric rare earths including Y, Sm, Eu, Gd, Tb, Dy, Ho, Er, Tm, Yb and Lu.

In the process of the invention, the following rare earths are envisaged more particularly: lanthanum, ytterbium, lutetium and/or scandium.

The triflates of rare earths are known products which are described in the literature, particularly in U.S. Pat. No. 3 615 169. They are generally obtained by reaction of the rare earth oxide and trifluoromethane sulfonic acid.

According to a variant of the process of the invention, the catalyst is advantageously prepared in situ by allowing trifluoromethane sulfonic acid to react with a source of rare earth.

The nature of the compounds providing the various elements used for the preparation of the catalyst of the invention is not critical.

The rare earth elements may be provided in the form of a metal or in the form of an inorganic derivative such as an oxide or a hydroxide. It is possible to use a mineral salt, preferably nitrate, sulfate, oxysulfate, halide, oxyhalide, silicate, carbonate, orthophosphate or an organic derivative, preferably oxalate, acetylacetonate; alcoholate or even more preferably methylate or ethylate; carboxylate or even more preferably acetate.

Preferably, use is made of nitrates, chlorides and/or sulfates of rare earths such as cerium, lanthanum, praseodymium, neodymium, samarium, gadolinium, ytterbium and yttrium.

By way of examples of compounds which may be used for the preparation of the catalysts of the invention, the following may be mentioned in particular:

yttrium (III) chloride, lanthanum (III) chloride, neodymium (III) chloride, samarium (III) chloride.

ytterbium (III) chloride.

The bismuth salts of triflic acid described in patent application PCT/FR96/01488 may also be used in the process of the invention. A method of preparation of the bismuth triflate is given below.

In accordance with the process of the invention, it is possible, according to a variant of the invention, to use a polar, aprotic organic solvent having certain polarity and basicity characteristics, the presence of said solvent being able to improve the yield and regioselectivity of the reaction.

A first class of solvents suitable for the invention are polar and weakly basic organic solvents, i.e. having a polarity such that its dielectric constant is greater than or equal to 20 and a basicity such that it has a "donor number" of less than 25.

Another type of solvents also suitable for the invention are weakly polar but basic organic solvents, i.e. having a polarity such that its dielectric constant is less than about 20 and a basicity such that it has a "donor number" greater than or equal to 15 and less than 25.

Several requirements govern the choice of the organic solvent.

A first characteristic of the organic solvent is that it be aprotic and stable in the reaction medium.

The term aprotic solvent means a solvent which, in Lewis theory, has no protons to release.

Excluded from the present invention are solvents which are not stable in the reaction medium and which are degraded either by oxidation or by hydrolysis. Examples of reaction solvents which are not suitable for the invention include solvents of the ester type derived from carboxylic acids such as, in particular, methyl or ethyl acetate, methyl or ethyl phthalate, methyl benzoate, etc.

The organic solvents suitable for use in the process of the invention must meet certain requirements in terms of their polarity and their basicity which is characterised by the donor number.

A first class of organic solvents highly suitable for use in the process of the invention are polar and weakly basic organic solvents.

In accordance with the invention, the organic solvent chosen has a dielectric constant greater than or equal to 20. The upper limit is not critical. It is preferable to use an organic solvent having a high dielectric constant, preferably between 25 and 75.

The organic solvent having the above-mentioned polarity characteristics must also satisfy certain basicity conditions. In fact, the said solvent must not be too basic. In order to determine whether a solvent satisfies this requirement, its basicity is assessed by reference to the "donor number". The polar organic solvent chosen has a donor number of less than 25. preferably less than or equal to 20. The lower-limit is not critical. In preference, an organic solvent having a donor number between 2 and 17 is chosen.

As regards the other class of claimed solvents, the characteristics of said solvents are defined below.

The solvents belonging to this category are weakly polar but basic organic solvents.

In accordance with the invention, the organic solvent chosen has a dielectric constant of less than about 20. The lower limit is not critical. It is preferable to use an organic solvent having a low dielectric constant, preferably between 2 and 15.

As regards its basicity, it must be such that it has a "donor number" greater than or equal to 15 and less than 25. In preference, an organic solvent having a donor number between 15 and 25 is chosen.

In order to determine whether the organic solvent meets the conditions of the dielectric constant set out above, reference may be may, inter alia, to the tables in the work: Techniques of Chemistry II—Organic solvents, p. 536 et seq., 3rd edition (1970).

With regard to the requirements concerning the basicity of the organic solvent to be used, reference is made to the definition of the "donor number" given above.

Examples of polar, aprotic organic solvents complying with the basicity characteristics mentioned above and which may be used in the process of the invention include more particularly:

nitrated compounds such as nitromethane, nitroethane, 1-nitropropane, 2-nitropropane or mixtures thereof, nitrobenzene, aliphatic or aromatic nitrites such as acetonitrile, propionitrile, butane nitrile, isobutane nitrile, benzonitrile, benzyl cyanide, tetramethylene sulfone (sulfolane), propylene carbonate, It is also possible to use a mixture of solvents.

Of the above-mentioned solvents, acetonitrile is used in preference.

As regards the other class of claimed solvents, examples of weakly polar and basic aprotic solvents suitable for use in the process of the invention are given below:

aliphatic, cycloaliphatic or aromatic ether oxides, and more particularly diethyl oxide, dipropyl oxide, diisopropyl oxide, dibutyl oxide, methyltertiobutylether, dipentyl oxide, diisopentyl oxide, ethylene glycol dimethylether (or 1,2-dimethoxyethane), diethylene glycol dimethylether (or 1,5-dimethoxy-3-oxapentane), dioxane, tetrahydrofuran, neutral phosphoric esters such as, in particular, trimethyl phosphate, triethyl phosphate, butyl phosphate, triisobutyl phosphate, tripentyl phosphate.

ethylene carbonate.

It is also possible to use a mixture of solvents.

According to another variant of the process of the invention, hydroxylation of the phenolic compound is carried out in the presence of a ketone compound, more particularly those corresponding to formula (II):

$$R_a\text{—CO—X—}R_b \quad (II)$$

in which formula (II):

$R_a$ and $R_b$, identical or different, represent hydrocarbon radicals having 1 to 30 carbon atoms or form together a divalent radical, optionally substituted by one or more halogen atoms or functional groups which are stable under the reaction conditions, X represents a valency bond, a —CO— group, a —CHOH group, or an $(-(R)_{-n}$ group representing an alkylene group preferably having 1 to 4 carbon atoms and n is an integer chosen between 1 and 16.

In formula (II), $R_a$ and $R_b$ represent more particularly:

linear or branched alkyl radicals, linear or branched alkenyl radicals, cycloalkyl or cycloalkenyl radicals containing 4 to 6 carbon atoms, mono- or polycyclic aryl radicals; in the latter case, the rings forming between them an ortho- or ortho- and pericondensed system or being linked together by a valency bond, arylalkyl or arylalkenyl radicals, $R_a$ and $R_b$ may together form an alkylene or alkenylene radical containing 3 to 5 carbon atoms, optionally substituted by an alkyl radical with low carbon condensation or by a cycloalkyl or cycloalkenyl radical having 4 to 6 carbon atoms; 2 to 4 carbon atoms of the alkylene or alkenylene radicals may form part of one or two benzene rings optionally substituted by 1 to 4 hydroxyl groups and/or alkyl groups and/or alkoxy groups with low carbon condensation.

In the description of the invention which follows, the term alkyl group with low carbon condensation means a linear or branched alkyl group generally having 1 to 4 carbon atoms.

The above-mentioned hydrocarbon radicals may be substituted by 1 or more, preferably 1 to 4 alkyl groups with low carbon condensation or functional groups such as hydroxyl groups, alkoxy groups with low carbon condensation, hydroxycarbonyl groups, alkyloxycarbonyl groups containing 1 to 4 carbon atoms in the alkyl group, a nitrile group, —SO₃H, nitro or by one or more halogen atoms, and particularly chlorine and bromine.

Preferably, $R_a$ and $R_b$ represent more particularly:

linear or branched alkyl radicals having 1 to 10 carbon atoms, linear or branched alkenyl radicals having 2 to 10 carbon atoms, cycloalkyl or cycloalkenyl radicals containing 4 to 6 carbon atoms, phenyl radicals optionally substituted by 1 to 4 alkyl and/or hydroxyl and/or alkoxy groups, phenylalkyl or phenylalkenyl radicals containing 1 (or 2) to 10 carbon atoms in the aliphatic part, and even more particularly 1 (or 2) to 5 carbon atoms in the aliphatic part, $R_a$ and $R_b$ may together form an alkylene or alkenylene radical containing 3 to 5 carbon atoms, optionally substituted by 1 to 4 alkyl radicals with low carbon condensation.

Specific examples of ketones which may be used in the process of the invention include, more particularly:

acetone
butan-2-one
methylisopropyl ketone
pivalone
pentan-2-one
pentan-3-one
4-methylpentan-2-one
3,3-dimethylbutan-2-one
hexan-2-one
hexan-3-one
heptan-2-one
heptan-4-one
octan-2-one
octan-3-one
nonan-2-one
nonan-5-one
pentadecan-8-one
2-methylhexan-3-one
5-methylhexan-2-one
5-methylhexan-3-one
4-dimethylpentan-3-one
5-methylheptan-3-one
methyl vinyl ketone
mesityl oxide
pent-1-en-3-one
pent-3-en-2-one
hex-5-en-2-one
5-methylhex-3en-one
6-methylhept-5-en-2-one
diacetyl
diacetone alcohol
acetoin
butane-2,3-dione
pentane-2,4-dione
hexane-2,5-dione
dicyclohexyl ketone
methylcyclohexyl ketone
acetophenone
n-propicphenone
n-butyrophenone
isobutyrophenone
n-valerophenone
2-methylacetophenone
2,4-dimethylacetophenone
phenyl vinyl ketone
benzophenone
2-methylbenzophenone
2,4-dimethylbenzophenone
4,4'-dimethybenzophenone
2,2'-dimethylbenzophenone
4,4'-dimethoxybenzophenone
4-hydroxybenzophenone
4,4'-dihydroxybenzophenone
benzoyl-4-biphenyl
benzoin
4,4'-dihydroxybenzoin
2,4-dimethylbenzoin 4,4'-dimethylbenzoin
4,4'-dimethoxybenzoin
4,4'-difluorobenzoin
α-methoxybenzoin
α-ethoxy benzoin
deoxybenzoin
4-hydroxydeoxybenzoin
4-methyldeoxybenzoin
4-methoxydeoxybenzoin
4,4'-imethoxydeoxybenzoin
4,4'-difluorodeoxybenzoin
β-phenylpropiophenone
dibenzyl ketone
o-phenytvalerophenone
1,1-diphenylpropan-2-one
1,3-diphenylpropanone
benzalacetone
benzalacetophenone
benzil
cyclopentanone
2-methylcyclopentanone
cyclohexanone
2-methylcyclohexanone
3,3,5,5-tetramethylcyclohexanone
cyclopenten-2-one
cyclohexen-2-one
α-isophorone
β-isophorone
cyclohexenyl cyclohexanone
α-indanone
β-indanone
α tetralone
fluorenone.

Thus, use is made of, more particularly, ketone compounds of the dialkyl ketone type corresponding to formula (II) in which $R_a$ and $R_b$ represent a linear or branched alkyl radical having 1 to 8 carbon atoms, and of alkylphenones, i.e. $R_a$ represents a linear or branched alkyl radical having 1 to 6 carbon atoms and $R_b$ represents a phenyl radical.

More specific examples of dialkyl ketones and alkylphenones include pentanones, acetophenone and n-valerophenone.

Of all the ketone compounds corresponding to formula (II), the ketone compounds corresponding to formula (IIa) below are used more particularly:

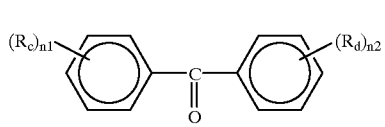

(IIa)

in which formula (IIa):

$R_c$ and $R_d$, identical or different, represent a hydrogen atom or a substituent, preferably an electro-donor group, $n_1$, $n_2$, identical or different, is a number equal to 0. 1, 2 or 3.

optionally the two carbon atoms situated in position a with respect to the two carbon atoms bearing the —CO group may be linked together by a valency bond or by a —CH$_2$— group thus forming a ketone ring which may be saturated but also unsaturated.

The substituent is chosen such that it does not react under the acidity conditions of the invention. It is preferably an electro-donor group.

The term "electro-donor group" means a group as defined by H. C. BROWN in the work by Jerry MARCH—Advanced Organic Chemistry, chapter 9, pages 243 and 244 (1985).

Examples of substituents suitable for the invention are as follows:

linear or branched alkyl radicals having 1 to 4 carbon atoms, the phenyl radical, alkoxy radicals $R_{10}$—O in which $R_{10}$ represents a linear or branched alkyl radical having 1 to 4 carbon atoms or the phenyl radical, the hydroxyl group, the fluorine atom.

Examples of ketone compounds particularly suitable for the invention include, more particularly, the ketone compounds corresponding to the general formula (IIa) in which $R_c$ and $R_d$, identical or different, represent a hydrogen atom or a substituent as mentioned above, preferably in the 4,4' position, and $n_1$, $n_2$, identical or different, are equal to 0 or 1.

The ketone compounds used in preference correspond to formula (IIa) in which $R_c$ and $R_d$, identical or different, represent a hydrogen atom, a methyl, ethyl, tert-butyl, phenyl radical, a methoxy or ethoxy radical, a hydroxyl group preferably in the 3.3' or 4,4 position.

Specific examples of ketones which may be used in the process of the invention include more particularly:

benzophenone
2-methylbenzophenone
2,4-dimethylbenzophenone
4,4'-dimethylbenzophenone
2,2'-dimethylbenzophenone
4,4'-dimethoxybenzophenone
4-hydroxybenzophenone
4,4'-dihydroxybenzophenone
benzoyl-4-biphenyl.

In accordance with the process of the invention, hydrogen peroxide, a catalyst, optionally an organic solvent and/or a ketone compound are used during the process for the hydroxylation of the phenolic compound of formula (I).

The hydrogen peroxide used according to the invention may be in the form of an aqueous solution or organic solution.

Aqueous solutions, being more readily available on the market, are used in preference.

The concentration of the aqueous solution of hydrogen peroxide, although not critical in itself, is chosen such as to introduce as little water as possible into the reaction medium. Generally, an aqueous solution of hydrogen peroxide containing at least 20 wt. % of $H_2O_2$ and preferably in the region of 70% is used.

The amount of hydrogen peroxide may be as much as 1 mole of $H_2O_2$ per 1 mole of phenolic compound of formula (I).

It is preferable, however, in order to obtain an industrially acceptable yield, to use a molar ratio of hydrogen peroxide/phenolic compound of formula (I) of 0.01 to 0.3 and preferably 0.05 to 0.10.

In order to have a sufficient rate of reaction, the initial water content of the medium is limited to 10 wt. % and preferably 5 wt. %.

The weight contents given are expressed with respect to the mixture of phenolic compound of formula (I)/hydrogen peroxide/water.

This initial water corresponds to the water introduced with the reagents, particularly with hydrogen peroxide.

The amount of catalyst expressed by the ratio between the number of moles of triflate and the number of moles of hydrogen peroxide ranges advantageously between $10^{-4}$ and $10^{-1}$, preferably between $10^{-3}$ and $5.10^{-3}$.

The amount of organic solvent to be used is determined as a function of the nature of the organic solvent chosen.

Thus, if a polar but weakly basic organic solvent is used, it is determined in such a way that the molar ratio between the number of moles of organic solvent and the number of moles of phenolic compound of formula (I) ranges between 0.1 and 2.0. preferably between 0.25 and 1.0.

If a weakly polar and basic organic solvent is used, the quantity used is determined in such a way that the molar ratio between the number of moles of organic solvent and the number of moles of phenolic compound of formula (I) ranges between 0.01 and 0.25, preferably between 0.025 and 0.15.

The ketone compound of formula (II) which was defined above is used in a quantity defined below.

Generally, the amount of ketone compound of formula (II) expressed in moles per mole of hydrogen peroxide ranges between $1.10^{-3}$ and 10. It is not necessary to exceed 1.0 mole of ketone compound per mole of hydrogen peroxide. In practice, the amount of ketone compound is most often between 0.05 and 1.0 mole per mole of hydrogen peroxide.

In accordance with the process of the invention, hydroxylation of the phenolic compound of formula (I) is carried out at a temperature which may be between 45° C. and 150° C.

A preferred variant of the process of the invention consists in choosing the temperature between 50° C. and 80° C.

The reaction is conducted advantageously under atmospheric pressure.

From a practical point of view, the process according to the invention is simple to use continuously or batchwise.

Preferably, the various reagents as follows are introduced in any order, phenolic compound of formula (I), catalyst, ketone compound of formula (II), organic solvent.

The reaction medium is brought to the desired temperature, then the hydrogen peroxide solution is added gradually.

At the end of the reaction, the unconverted phenolic compound and the ketone compound of formula (II) are separated from the hydroxylation products by the usual methods, particularly by distillation, and are returned to the reaction zone.

Some embodiments of the invention are given below.

Examples 1 to 11 which follow illustrate the invention without limiting its scope.

The test a is a comparative example.

In the examples, the following abbreviations mean:

$$TT = \frac{\text{number of moles of hydrogen peroxide converted}}{\text{number of moles of hydrogen peroxide introduced}}\%$$

$$RT_{HQ} = \frac{\text{number of moles of hydroquinone formed}}{\text{number of moles of hydrogen peroxide converted}}\%$$

$$RT_{PC} = \frac{\text{number of moles of pyrocatechol formed}}{\text{number of moles of hydrogen peroxide converted}}\%$$

EXAMPLES

The operating protocol which is going to be followed in all the examples is given below.

The phenol and the catalyst, rare earth or bismuth triflate, optionally the ketone compound corresponding to formula (II), and the solvent are charged to a too ml glass flask fitted with a central stirrer, a cooling medium, dropping funnel and thermometer.

The various quantities used are indicated in the summary tables attached.

The reaction mixture is brought to the chosen reaction temperature, i.e. 75° C. whilst maintaining agitation at 1200 rpm.

Using the dropping funnel, the 70.5 wt. % aqueous solution of hydrogen peroxide is introduced in 2 minutes in a quantity also specified in the following tables.

The reaction mixture is kept under agitation at 75° C. for the period given in the following tables.

The reaction mixture is then cooled and the reaction products are determined: the residual hydrogen peroxide is determined by iodometry and the diphenols formed are determined by high performance liquid chromatography.

Examples 1 to 6

Comparative Test a

In this series of examples, various catalysts were used, namely:

ytterbium triflate: Examples 1, 5 and 6, lanthanum triflate: Example 2, scandium triflate: Example 3, lutetium triflate: Example 4.

The tests are conducted according to the operating protocol defined above.

All the conditions and the results obtained are summarised in Table (I) below:

TABLE I

| Ref. | Catalyst (mmol) | Phenol (g) | H$_2$O$_2$ (mmol) | H$_2$O (g) | Solvent (g) | Time (h) | TT (%) | RT (HQ) (%) | RT (PC) (%) | HQ/PC |
|---|---|---|---|---|---|---|---|---|---|---|
| 1 | Yb(OTf)$_3$ = 0.0334 mmol<br>benzophenone = 6.7 mmol | 23.5 | 11.5 | without | acetonitrile (2.5 g) | 2 | 98 | 45 | 39.5 | 1.14 |
| 2 | La(OTf)$_3$ × H$_2$O = 0.035 mmol<br>benzophenone = 6.6 mmol | 23.5 | 12.9 | without | acetonitrile (2.8 g) | 3 | 91.5 | 43.5 | 38 | 1.14 |
| 3 | Sc(OTf)$_3$ = 0.036 mmol<br>benzophenone = 6.5 mmol | 23.5 | 11.2 | without | acetonitrile (2.5 g) | 1 | 98 | 33.5 | 35 | 0.96 |
| 4 | Lu(OTf)$_3$ = 0.032 mmol<br>benzophenone = 6.5 mmol | 23.5 | 11.7 | without | acetonitrile (2.5 g) | 3 | 99 | 43 | 39.5 | 1.09 |
| 5 | Yb(OTf)$_3$ = 0.036 mmol<br>benzophenone = 6.5 mmol | 23.6 | 12.0 | without | acetonitrile (2.6 g) | 3 | 79.5 | 28 | 34.5 | 0.81 |
| 6 | Yb(OTf)$_3$ = 0.031 mmol<br>benzophenone = 6.6 mmol | 23.5 | 11.8 | without | without | 2 | 99 | 16 | 33 | 0.48 |
| a | Mg(OTf)$_2$ = 0.069 mmol<br>benzophenone = 6.6 mmol | 23.2 | 11.25 | without | acetonitrile (2.5 g) | 3 | 17 | 24 | 26 | 0.92 |

By way of comparison, the results obtained are given for the case when the process of the invention is carried out in the presence of magnesium triflate (test a).

An examination of Table (1) clearly shows that the presence of the catalyst, the ketorte and the organic solvent as defined leads to the best results in terms of yield and para-selectivity.

Example 7

In this example, less catalyst, scandium triflate, was used.

A comparison of Examples 7 and 3 shows that the reduction in the amount of catalyst leads to an increase in the yield and selectivity of the reaction in favour of hydroquinone.

The test is carried out according to the operating protocol defined above.

All the conditions and the results obtained are summarised in Table (II) below.

Example 8

In this example, the effect of the organic solvent was illustrated.

A comparison of Examples 8 and 1 shows that the use of a solvent leads to an increase in the yield and selectivity of the reaction in favour of hydroquinone.

The test is carried out according to the operating protocol defined above.

All the conditions and the results obtained are summarised in Table (III) below:

TABLE II

| Ref. | Catalyst (mmol) | Phenol (g) | H$_2$O$_2$ (mmol) | H$_2$O (g) | Solvent (g) | Time (h) | TT (%) | RT (HQ) (%) | RT (PC) (%) | HQ/PC |
|---|---|---|---|---|---|---|---|---|---|---|
| 7 | Sc(OTf)$_3$ = 0.013 mmol<br>benzophenone = 6.6 mmol | 23.5 | 12.2 | without | acetonitrile (2.6 g) | 2 | 95.5 | 40.5 | 37.5 | 1.08 |
| 3 | Sc(OTf)$_3$ = 0.038 mmol<br>benzophenone = 6.6 mmol | 23.5 | 11.2 | without | acetonitrile (2.5 g) | 1 | 98 | 33.5 | 35 | 0.96 |

TABLE III

| Ref. | Catalyst (mmol) | Phenol (g) | H$_2$O$_2$ (mmol) | H$_2$O (g) | Solvent (g) | Time (h) | TT (%) | RT (HQ) (%) | RT (PC) (%) | HQ/PC |
|---|---|---|---|---|---|---|---|---|---|---|
| 8 | Yb(OTf)$_3$ = 0.035 mmol<br>benzophenone = 6.4 mmol | 23.5 | 12.5 | without | without | 1 | 98 | 27.5 | 34.5 | 0.80 |
| 1 | Yb(OTf)$_3$ = 0.0334 mmol<br>benzophenone = 6.7 mmol | 23.5 | 11.5 | without | acetonitrile (2.5 g) | 2 | 98 | 45 | 39.5 | 1.14 |
| 6 | Yb(OTf)$_3$ = 0.031 mmol<br>benzophenone = 6.6 mmol | 23.5 | 11.8 | without | without | 2 | 99 | 16 | 33 | 0.48 |

Examples 9 and 10

In the examples that follow, a different ketone compound is used, namely acetophenone.

The tests are carried out according to the operating protocol defined above.

All the conditions and the results are summarised in Table (IV) below.

TABLE IV

| Ref. | Catalyst (mmol) | Phenol (g) | $H_2O_2$ (mmol) | $H_2O$ (g) | Solvent (g) | Time (h) | TT (%) | RT (HQ) (%) | RT (PC) (%) | HQ/PC |
|---|---|---|---|---|---|---|---|---|---|---|
| 9 | $Yb(OTf)_3$ = 0.035 mmol<br>acetophenone = 7.5 mmol | 26 | 13.9 | without | acetonitrile (2.6) | 0 h 30 | 100 | 39 | 47.5 | 0.82 |
| 10 | $Yb(OTf)_3$ = 0.032 mmol<br>acetophenone = 6.4 mmol | 23.5 | 13.1 | without | without | 1 | 100 | 35 | 47 | 0.74 |

TABLE V

| Ref. | Catalyst (mmol) | Phenol (g) | $H_2O_2$ (mmol) | $H_2O$ (g) | Solvent (g) | Time (h) | TT (%) | RT (HQ) (%) | RT (PC) (%) | HQ/PC |
|---|---|---|---|---|---|---|---|---|---|---|
| 11 | $Bi(OTf)_3$ = 0.034 mmol<br>benzophenone = 6.4 mmol | 23.8 | 12.5 | without | acetonitrile (2.5) | 2 | 98 | 18.5 | 22 | 0.84 |

Example 11

In this example, bismuth triflate is used as catalyst.

The latter may be prepared as follows:

0.44 g of triphenylbismuth $Ph_3Bi$ (1 mmol) and 10 ml of anhydrous dichloromethane are introduced, with stirring, into a 250 ml flask purged with argon and fitted with an air inlet connected to a calcium chloride tube.

The solution is cooled to −78° C.

Using a syringe, 0.44 g of triflic acid (2.9 mmol) are added.

A yellow colour appears.

The reaction mixture is left to cool to ambient temperature.

The solid obtained is filtered under argon and washed with dry dichloromethane in order to remove the traces of triflic acid.

The power is introduced into a two-neck flask and dried under reduced pressure (18 mm of mercury), under argon, for 1 hour.

The use of said catalyst for hydroxylating phenol is carried out according to the operating protocol defined above.

All the conditions and the results obtained are summarised in Table (V) above.

What is claimed is:

1. A process for hydroxylating a phenolic compound with hydrogen peroxide through a hydroxylation reaction, comprising the step of carrying out said hydroxylation reaction in the presence of an effective quantity of a catalyst to catalyze said hydroxylation reaction comprising a triflate of a rare earth element, of scandium or of bismuth, wherein the phenolic compound corresponds to the general formula (I):

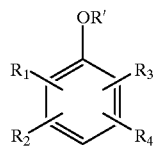

(I)

wherein:

R' represents a hydrogen atom, a saturated or unsaturated linear or branched acyclic or aliphatic hydrocarbon radical having 1 to 24 carbon atoms, a saturated or unsaturated monocyclic or polycyclic cycloaliphatic radical, or a saturated or unsaturated linear or branched aliphatic radical bearing a cyclic substituent, and $R_1, R_2, R_3$ and $R_4$, are identical or different, and represent:

a hydrogen atom, a linear or branched alkyl radical having 1 to 6 carbon atoms, a linear or branched alkenyl radical having 2 to 6 carbon atoms, a linear or branched alkoxy radical having 1 to 6 carbon atoms, an acyl group having 2 to 6 carbon atoms, or a radical having the formula:

$R_5$—OH, $R_5$—$COOR_6$, $R_5$—X, or $R_5$—$CF_3$, wherein $R_5$ represents a valency bond or a linear or branched, saturated or unsaturated divalent hydrocarbon radical having 1 to 6 carbon atoms; $R_6$ represents a hydrogen atom or a linear or branched alkyl radical having 1 to 6 carbon atoms;

x represents a halogen atom, optionally, two groups $R_1$ and $R_2$ and $R_3$ and $R_4$ placed on two vicinal carbon atoms, together and with the carbon atoms bearing them, form a benzene ring.

2. A process according to claim 1, wherein the rare earth element is selected from the group consisting of lanthanides, yttrium, and mixtures thereof.

3. A process according to claim 2, wherein the lanthanides is selected from the group consisting of lanthanum, cerium, praseodymium, neodymium, samarium, europium, gadolinium, terbium, dysprosium, holmium, erbium, thulium, ytterbium, lutetium, and mixtures thereof.

4. A process according to claim 1, wherein the catalyst is a triflate of at least one ceric rare earth selected from the group consisting of La, Ce, Pr, and Nd.

5. A process according to claim 1, wherein the catalyst is a triflate of at least one rare earth element selected from the group consisting of Sm, Eu, Gd, Tb, Dy, Ho, Er, Tm, Yb and Lu.

6. A process according to claim 1, wherein the rare earth element is lanthanum, ytterbium, or lutetium.

7. A process according to claim 1, further comprising the step of carrying out the hydroxylation reaction in the presence of an organic solvent.

8. A process according to claim 7, wherein the solvent is a polar, aprotic organic solvent having a polarity such that its dielectric constant is greater than or equal to 20 and a basicity such that it has a donor number of less than 25.

9. A process according to claim 8, wherein the polar organic solvent has a dielectric constant between 25 and 75.

10. A process according to claim 8, wherein the polar organic solvent has a donor number of less than or equal to 20.

11. A process according to claim 8, wherein the polar organic solvent is a nitrated compound, an aliphatic nitrile, an aromatic nitrile, tetramethylene sulfone, or propylene carbonate.

12. A process according to claim 11, wherein the polar organic solvent is nitromethane, nitroethane, 1-nitropropane, 2-nitropropane, nitrobenzene, acetonitrile, propionitrile, butane nitrile, isobutane nitrile, benzonitrile, or benzyl cyanide.

13. A process according to claim 7, wherein the molar ratio between the number of moles of organic solvent and the number of moles of phenolic compound ranges between 0.1 and 2.0.

14. A process according to claim 8, wherein the molar ratio is between 0.25 and 1.0.

15. A process according to claim 2, wherein the reaction is earned out in the presence of a polar, aprotic organic solvent having a polarity such that its dielectric constant is less than about 20 and a basicity such that it has a donor number greater than or equal to 15 and less than 25.

16. A process according to claim 15, wherein the polar organic solvent has a dielectric constant between 2 and 15.

17. A process according to claim 15, wherein the polar organic solvent has a donor number between 15 and 25.

18. A process according to claim 15, wherein the polar organic solvent is an aliphatic ether oxide, a cycloaliphatic ether oxide, an aromatic ether oxide, a neutral phosphoric ester, or ethylene carbonate.

19. A process according to claim 18, wherein the polar organic solvent is diethyl oxide, dipropyl oxide, diisopropyl oxide, dibutyl oxide, methyltert butyl ether, dipentyl oxide, diisopentyl oxide, ethylene glycol dimethyl ether diethylene glycol dimethyl ether dioxane, terahydrofuran, trimethyl phosphate, triethyl phosphate, butyl phosphate, triisobutyl phosphate, or tripentyl phosphate.

20. A process according to claim 15, wherein the molar ratio between the number of moles of organic solvent and the number of moles of phenolic compound ranges between 0.01 and 0.25.

21. A process according to claim 20, wherein the molar ratio is between 0.025 and 0.15.

22. A process according to claim 1, further comprising the step of carrying out the reaction in the presence of a ketone compound.

23. A process according to claim 22, wherein the ketone compound corresponds to formula (II):

$$R_a\text{—CO—X—}R_b \qquad (II)$$

wherein:
$R_a$ and $R_b$, identical or different, represent hydrocarbon radicals having 1 to 30 carbon atoms or form together a divalent radical, optionally substituted by one or more halogen atoms or functional groups which are stable under the reaction conditions, and X represents a valency bond, a —CO— group, a —CHOH group, or a (—(R)$_n$) group, R representing an alkylene group, and n is an integer between 1 and 16.

24. A process according to claim 23, wherein the ketone corresponds to formula (II) in which $R_a$ and $R_b$ represent:
linear or branched alkyl radicals,
linear or branched alkenyl radicals,
cycloalkyl or cycloalkenyl radicals containing 4 to 6 carbon atoms,
mono- or polycyclic aryl radicals; in the latter case, the rings forming between them an ortho- or ortho- and pericondensed system or being linked together by a valency bond, arylalkyl or arylalkenyl radicals, or
$R_a$ and $R_b$ together optionally form an alkylene or alkenylene radical containing 3 to 5 carbon atoms, optionally substituted by an alkyl radical or by a cycloalkyl or cycloalkenyl radical having 4 to 6 carbon atoms; 2 to 4 carbon atoms of the alkylene or alkenylene radicals optionally form part of one or two benzene rings optionally substituted by 1 to 4 hydroxyl or alkyl or alkoxy groups.

25. A process according to claim 23, wherein the ketone compound is a dialkylketone corresponding to formula (II) wherein $R_a$ and $R_b$ represent a linear or branched alkyl radical having 1 to 8 carbon atoms or an alkylphenone corresponding to formula (II) wherein $R_a$ represents a linear or branched alkyl radical having 1 to 6 carbon atoms and $R_b$ represents a phenyl radical.

26. A process according to claim 25, wherein the ketone compound used corresponds to formula (IIa):

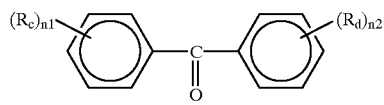

wherein;
$R_c$ and $R_d$, identical or different, represent a hydrogen atom or a substituent, optionally being an electo-donor group,
$n_1$, $n_2$, identical or different, is a number equal to 0, 1, 2 or 3, and optionally the two carbon atoms situated in position a with respect to the two carbon atoms bearing the —CO group are linked together by a valency bond or by a —CH$_2$— group thus forming a ketone ring.

27. A process according to claim 26, wherein the ketone compound corresponds to the general formula (IIa) in which $R_c$ and $R_d$, identical or different, represent:
linear or branched alkyl radicals having 1 to 4 carbon atoms,
a phenyl radical,
an alkoxy radical $R_{10}$—O in which $R_{10}$ represents a linear or branched alkyl radical having 1 to 4 carbon atoms or the phenyl radical,
a hydroxyl group, and
a fluorine atom.

28. A process according to claim 26, wherein the ketone compound corresponds to the general formula (IIa) in which $R_c$ and $R_d$, identical or different, represent a hydrogen atom or $R_c$ and $R_d$ are electro-donor groups in the 4,4' position, and $n_1$, $n_2$, identical or different, are equal to 0 or 1.

29. A process according to claim 26, wherein the ketone compound corresponds to the general formula (IIa) in which $R_c$ and $R_d$, identical or different, represent a hydrogen atom; a methyl, ethyl, tert-butyl, phenyl radical, a methoxy or ethoxy radical, or a hydroxyl group.

30. A process according to claim 29, wherein the hydroxyl groups are in the 3,3' or 4,4' position.

31. A process according to claim 22, wherein the ketone compound is acetone, 3,3-dimethylbutan-2-one, methyl vinyl ketone, mesityl oxide, 2,4-dimethylpentan-3-one, diacetyl, dicyclohexyl ketone, acetophenone, benzophenone, 2-methylbenzophenone, 2,4-dimethylbenzophenone, 4,4'-dimethylbenzophenone, 2,2'-dimethylbenzophenone, 4,4'-dimethoxybenzophenone, 4-hydroxybenzophenone, 4,4'-dihydroxybenzophenone, benzoyl-4-biphenyl, benzoin, 4,4'-dihydroxybenzoin, 2,4-dimethylbenzoin, 4,4'-diimethylbenzoin, 4,4'-dimethoxybenzoin, 4,4'-difluorobenzoin, a-methoxy benzoin, α-ethoxybenzoin, deoxybenzoin, 4-hydroxydeoxybenzoin, 4-methyldeoxybenzoin, 4-methoxydeoxybenzoin, 4,4'-dimethoxydeoxybenzoin, 4,4'-difluorodeoxybenzoin, benzalacetone, benzil, cyclohexanone, α-isophorone, cyclohexenyl cyclohexanone, or fluorenone.

32. A process according to claim 1, wherein the phenolic compound corresponds to the general formula (I) wherein:
R' represents:
a hydrogen atom,
a linear or branched alkyl radical having 1 to 4 carbon atoms,
a cyclohexyl radical, or
a benzyl radical,
$R_1$, $R_2$, $R_3$ and $R_4$, identical or different, represent:
a hydrogen atom,
a linear or branched alkyl radical having 1 to 4 carbon atoms,
a linear or branched alkoxy radical having 1 to 4 carbon atoms,
a hydroxyl group,
a halogen atom,
a —$CF_3$ group,
a cyclohexyl radical, or
a phenyl radical,
optionally two groups $R_1$ and $R_2$ or $R_3$ and $R_4$ placed on two vicinal carbon atoms, together and with the carbon atoms bearing them, form a benzene ring.

33. A process according to claim 1, wherein R' represents a hydrogen atom and one of the radicals $R_1$, $R_2$, $R_3$ and $R_4$ represents a hydroxyl group, a methyl radical or a methoxy radical and the 3 others represent a hydrogen atom.

34. A process according to claim 1, wherein the phenolic compound is phenol, anisole, o-cresol, m-cresol and p-cresol.

35. A process according to claim 1, wherein the catalyst is present in an amount expressed by the ratio between the number of moles of triflate and the number of moles of hydrogen peroxide, ranging between $10^{-4}$ and $10^{-1}$.

36. A process according to claim 35, wherein said ratio is between $10^{-3}$ and $5 \times 10^{-3}$.

37. A process according to claim 1, wherein the molar ratio hydrogen peroxide/phenolic compound of formula (I) is between 0.01 and 0.3.

38. A process according to claim 37, wherein said ratio is between 0.05 and 0.10.

39. A process according to claim 22, wherein the amount of ketone compound is between $1 \times 10^{-3}$ mole and 10 moles per mole of hydrogen peroxide.

40. A process according to claim 22, wherein the amount of ketone compound is between 0.05 and 1.0 mole per mole of hydrogen peroxide.

41. A process according to claim 1, wherein the hydroxylation reaction is carried out at a temperature between 45° C. and 150° C.

42. A process according to claim 41, wherein the temperature is between 50° C. and 80° C.

* * * * *